United States Patent [19]

Miller et al.

[11] Patent Number: 5,679,302
[45] Date of Patent: Oct. 21, 1997

[54] METHOD FOR MAKING A MUSHROOM-TYPE HOOK STRIP FOR A MECHANICAL FASTENER

[75] Inventors: Philip Miller, Eagan; William L. Melbye, Woodbury; Susan K. Nestegard, Woodbury; Leigh E. Wood, Woodbury, all of Minn.; Marvin D. Lindseth, Prescott, Wis.; Dale A. Bychinski, Woodbury, Minn.

[73] Assignee: Minnesota Mining and Manufacturing Company, St. Paul, Minn.

[21] Appl. No.: 48,874

[22] Filed: Apr. 16, 1993

Related U.S. Application Data

[60] Continuation-in-part of Ser. No. 789,594, Nov. 8, 1991, Pat. No. 5,607,635, which is a division of Ser. No. 585,990, Sep. 21, 1990, Pat. No. 5,077,870.

[51] Int. Cl.$^6$ .................................................... D01D 5/20
[52] U.S. Cl. ................................................................ 264/167
[58] Field of Search ............................................... 264/167

[56] References Cited

U.S. PATENT DOCUMENTS

| | | | |
|---|---|---|---|
| 2,717,437 | 9/1955 | Mestral | 28/72 |
| 3,009,235 | 11/1961 | Mestral | 28/78 |
| 3,027,595 | 4/1962 | Takai et al. | |
| 3,147,528 | 9/1964 | Erb | 24/204 |
| 3,192,589 | 7/1965 | Pearson | 24/204 |
| 3,235,438 | 2/1966 | Wisotzky | 161/62 |
| 3,270,408 | 9/1966 | Nealis | 29/408 |
| 3,312,583 | 4/1967 | Rochlis | 161/62 |
| 3,408,705 | 11/1968 | Kayser et al. | 24/204 |
| 3,555,601 | 1/1971 | Price | |
| 3,594,863 | 7/1971 | Erb | |
| 3,594,865 | 7/1971 | Erb | |
| 3,718,725 | 2/1973 | Hamano | 264/163 |
| 3,762,000 | 10/1973 | Meazin et al. | 24/204 |
| 4,290,174 | 9/1981 | Kalleberg | 24/204 |
| 4,315,885 | 2/1982 | Lemelson | 264/297 |
| 4,454,183 | 6/1984 | Wollman | 428/100 |
| 4,872,243 | 10/1989 | Fischer | 264/167 |
| 5,077,870 | 1/1992 | Melbye et al. | 24/452 |

FOREIGN PATENT DOCUMENTS

| | | |
|---|---|---|
| 270733 | 5/1964 | Australia . |
| 0 324 577 | 7/1989 | European Pat. Off. . |
| 0 325 528 | 7/1989 | European Pat. Off. . |
| 1383501 | 11/1964 | France . |
| A 3 244 410 | 10/1983 | Germany . |
| WO87/06522 | 11/1987 | WIPO . |

OTHER PUBLICATIONS

PCT Search Report for PCT/US91/105874 (corresponding to U.S. 07/585,990) of which this application is a division.
*Injection Molding Handbook*, edited by Dominick V. Rosato et al, Van Nostand Reinhold Co., New York: 1968, pp. 504–506, 596, 619–621, 753–756.

Primary Examiner—Karen Aftergut
Attorney, Agent, or Firm—Gary L. Griswold; Walter N. Kirn; William L. Huebsch

[57] ABSTRACT

A mushroom-type hook strip that can be used in a hook-and-loop mechanical fastener. The hook strip includes a homogeneous backing of thermoplastic resin and, integral with the backing, a high density array of hooks including stems projecting from the backing and circular disc shaped heads at the ends of the stems opposite the backing. The large number, small size, and shape of the heads on the hooks allow them to engage the fibers in conventional types of fabrics and non-woven materials that are not normally used as the loop portions of hook and loop fasteners.

9 Claims, 3 Drawing Sheets

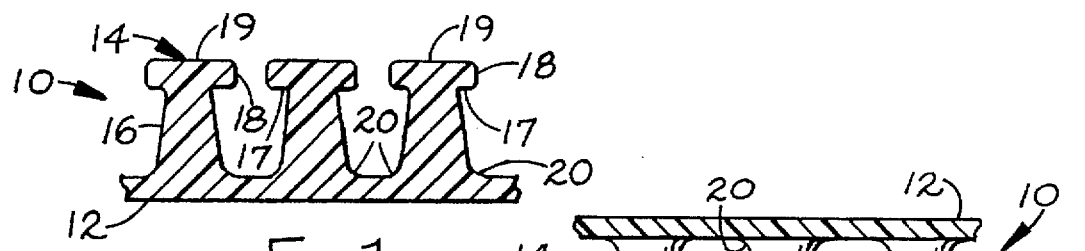
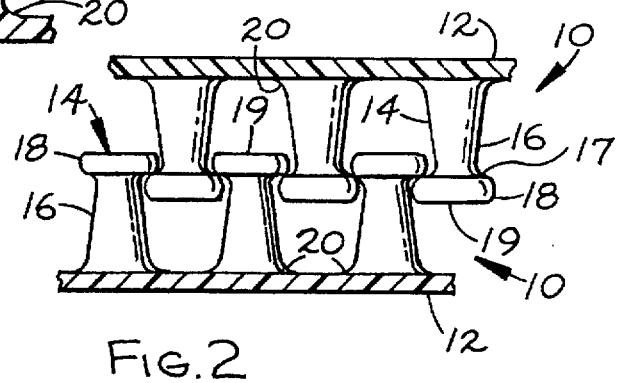
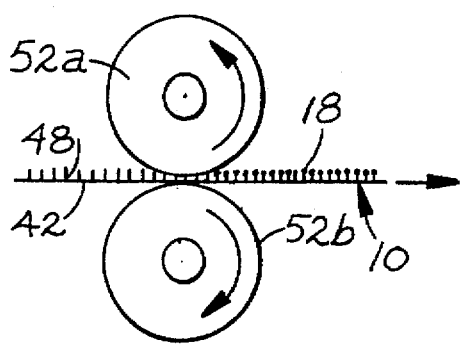
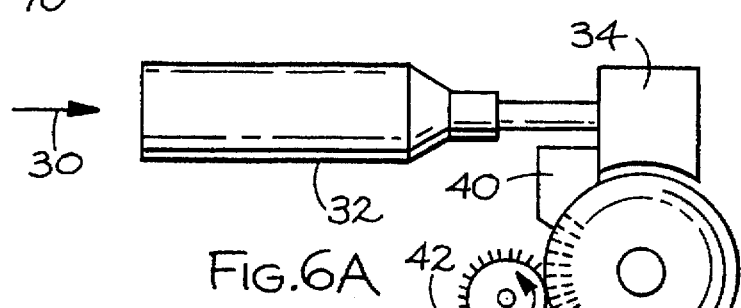
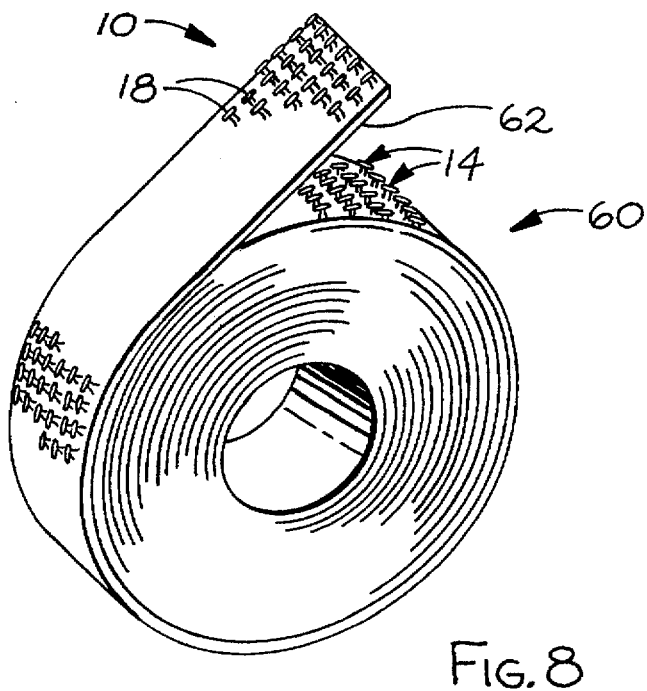

METHOD FOR MAKING A MUSHROOM-TYPE HOOK STRIP FOR A MECHANICAL FASTENER

CROSS REFERENCE TO RELATED APPLICATIONS

This application is a continuation-in-part of U.S. patent application Ser. No. 07/789,594 filed Nov. 8, 1991, now U.S. Pat. No. 5,607,635, which is a division of U.S. patent application Ser. No. 07/585,990 filed Sep. 21, 1990, now U.S. Pat. No. 5,077,870, the content whereof is incorporated herein by reference.

BACKGROUND OF THE INVENTION

1. Field of the Invention

The invention concerns mechanical fasteners such as hook-and-loop fasteners and is especially concerned with a mushroom-type hook strip such as can releasably close a garment, e.g., a disposable garment such as a diaper or a hospital gown. The invention also concerns mushroom-type hermaphroditic mechanical fasteners.

2. Description of the Related Art

Widely used as garment fasteners are hook-and-loop fasteners such as are currently marketed under the trademark VELCRO by Velcro USA Inc. and under the trademark SCOTCHMATE by 3M Co. As taught in U.S. Pat. Nos. 2,717,437 and 3,009,235 (both DeMestral), the hook strip can be made from special warps of upstanding nylon loop pile. One leg of each loop is cut to leave an open-ended hook, which is available to act as a fastening element.

U.S. Pat. No. 3,594,865 (Erb) of American Velcro Inc. describes injection molding techniques for manufacturing the hook strip of a hook-and-loop fastener. This, it says, provides "production rates which are faster than the weaving techniques required in U.S. Pat. Nos. 2,717,437 and 3,009,235." The Erb techniques employ a closed loop of a large number of shallow wire dies. While applying a vacuum to evacuate the wire dies, the closed loop is passed through an extruder by which molten plastic such as nylon is forced through the dies to impregnate a fabric web immediately beneath the dies. Upon exiting from the extruder, excess resin is stripped from the surfaces of the dies to leave resilient hooks that are progressively cammed out of the dies and then spring back to provide an orderly array of hooks projecting from the plastic impregnated fabric web. Instead of using a fabric web, the apparatus can be modified to create a space beyond the wire dies into which the molten plastic can flow to form an all-plastic backing for the hooks. Another Erb U.S. Pat. No. 3,594,863 concerns similar apparatus for producing a similar hook-bearing strip. In spite of these Erb patents, the hook strips of "Velcro" hook-and-loop fasteners, as marketed today, are predominantly made by weaving techniques.

Another procedure for continuously molding a hook strip is described in U.S. Pat. No. 3,762,000 (Meazin et al.).

In U.S. Pat. No. 3,718,725 (Hamano), the hook strip of a hook-and-loop fastener is made from a fabric having an orderly array of upstanding loops. After inserting rods into rows of loops to maintain their upstanding position, platens or rollers apply heat and pressure to melt each loop at its summit and to press each free molten end to form a knob or head that can interengage with the loop strip of a hook-and-loop fastener. Because the knobs or heads afford a mushroom appearance, this type of hook fastener is called "mushroom-type".

Although a hook strip of a hook-and-loop fastener is typically sold with a cooperating loop strip, the hook strip can be used by itself to become releasably fastened to fabrics that can be easily penetrated by the hooks. Mushroom-type hook strips are particularly suited for such use. For example, mushroom-type hook strips can be designed to become releasably fastened to burlap, terry cloth, and tricot.

Mushroom-type mechanical fasteners are sometimes designed so that two hook strips can be used to fasten two articles together by adhering each strip to one of the articles and then interengaging the two strips. Such a mushroom-type mechanical fastener is shown in U.S. Pat. No. 3,192,589 (Pearson) which calls the fastener "hermaphroditic" because its headed studs have both male and female characteristics when intermeshed. The Pearson fasteners can be made by molding a base from which integral headless studs project and then heat softening the tips of the studs.

The hermaphroditic mushroom-type mechanical fastener shown in U.S. Pat. No. 4,290,174 (Kalleberg) is made with flexible, resilient, U-shaped monofilaments. The bight portion of each monofilament is embedded in a flexible bonding layer so that two stems project normally from the surface of the bonding layer. There is a mushroom head at the tip of each stem. The stems preferably are substantially uniformly spaced and of substantially equal length. Maximum disengagement force is achieved when the spacing between adjacent heads is less than their diameters and the minimum required for engagement. The monofilaments preferably are longitudinally oriented polyolefin, and the bonding layer preferably is polyolefin to permit the monofilaments to be heat fused into the bonding layer.

U.S. Pat. No. 3,408,705 (Kayser et al.) shows mushroom-type mechanical fasteners having mushroom heads of several shapes.

SUMMARY OF THE INVENTION

The invention provides a mushroom-type hook strip for a mechanical fastener such as a hook-and-loop fastener, which hook strip, because of the density and shape of its hooks, affords the advantage over known prior mushroom-type hook strips of making better engagement in shear with certain types of conventional fabrics and loop materials than known mushroom-type hook strips, while being less expensive to manufacture. Like prior mushroom-type hook strips, that of the invention either can be used with a loop strip or can be directly fastened to a fabric that can be penetrated by the hooks.

In another aspect of the invention, the spacing of the mushroom-type hooks can be configured such that two pieces of the hook strip interengage to provide a mechanical fastener.

Briefly, the novel mushroom-type hook strip comprises a homogeneous backing of thermoplastic resin and, integral with backing, an array of upstanding stems distributed across at least one face of the backing, each having a mushroom head, said stems having a molecular orientation as evidenced by a birefringence value of at least 0.001, and the mushroom heads having circular disc shapes with generally planar end surfaces opposite the backing, which disc shaped heads preferably have diameter to thickness ratios of greater than about 1.5 to 1.

A novel method of making the mushroom-type hook strip employs a mold which can be cylindrical and has cavities recessed from a continuous surface that are the negatives of an array of upstanding stems. The novel method involves the steps of a) moving the surface of the mold along a predetermined path, b) continuously injecting a molten, molecularly orientable thermoplastic resin into the cavities in excess of the amount that would fill the cavities, which excess forms a layer of resin overlying the cavities and the surface around the cavities, c) continuously cooling the mold around the cavities to cause the molten resin to become molecularly oriented while it fills the cavities, d) allowing the injected resin to solidify, e) continuously stripping from the mold the solidified resin layer as a backing and integral array of upstanding stems, and f) deforming the tips of the stems by contact with a heated surface to produce a circular disc shaped mushroom head at the tip of each stem.

When the end of each of the cavities is closed, the method can further include an evacuating step that can involve the application of a vacuum so that the resin injected in step b) can substantially fill each cavity, all of which should have substantially equal depth. Alternatively, the cavities can have depths significantly longer than the lengths of the stems being formed so that the resin injected in step b) can compress the air in the cavities.

When the inner end of each cavity is open, the resin injected in step b) can evacuate the cavities. Additionally, a vacuum can be applied at the inner end of the cavities to enhance their filling. When, optionally, the injected resin flows beyond the open ends of the cavities, the protruding resin can be skived off at the ends of the cavities before the stripping step e), thus producing stems of uniform height when the cavities are of uniform depth.

In order to afford the desired molecular orientation, the walls of the cavities should be cooled to a temperature such that the injected resin solidifies along the walls while continuing to fill the core of each cavity. After the core of a cavity has been filled, the cooling must be continued to maintain the molecular orientation and to allow the stem to be pulled from the cavity. Afterwards, it may be desirable to apply heat to the wall of the cavity before it is again injected with resin.

The cavities can be tapered to a smaller diameter in the direction of injection to facilitate removal in step e). The cavities preferably are generally circular in cross section and have a draft angle of up to 15 degrees. The draft angle is the included angle between the axis of the cavity and its wall. When the cavities have open ends or have excessive depth so that air within the cavity is compressed as the resin in injected, tapering is of less significance, because the stripping step e) does not need to overcome a vacuum.

Because the stems of the novel hook strip are molecularly orientated as evidenced by a birefringence value of at least 0.001, they have significantly greater stiffness and durability, as well as greater tensile and flexural strength, than would be achievable without such orientation. Because of these qualities, the portions of the stems not heated by the heated surface remain resiliently flexible during the deforming step f) which preferably involves the application of heat to the stem tips by contact with the heated surface of a metal roller. Such contact forms the tip of each stem into a circular disc shaped mushroom head at the tip of each stem, which head has a substantially flat inner surface that enhances its holding power when engaged with a loop.

As compared to hook strips that have unoriented stems, the enhanced strength of the hooks of the novel hook strip makes them less likely to break during disengagement. When the novel hook strip is used with a loop strip, the enhanced strength of the hooks makes them less likely to break under disengagement forces than the loops, a beneficial attribute for at least two reasons. First, broken hooks can create debris whereas a broken loop does not. Furthermore, a loop strip typically contains many more loops than there are hooks per unit area, thus allowing a greater number of disengagements before a hook-and-loop fastener becomes useless.

Because of their circular, generally flat to slightly concave outer surfaces, the mushroom heads of the novel hook strip are user friendly and nonabrasive to the skin, thus making them ideally suited as closures for baby diapers. In such use, they are unaffected by talcum powder which can destroy the holding power of a pressure-sensitive adhesive diaper closure.

Although the stems of the novel hook strip preferably are generally circular in cross section, other suitable cross sections include rectangular and hexagonal. The stems preferably have fillets at their bases, both to enhance strength and stiffness and for easy release from a mold in which they are formed.

The disc-like head shape with its high diameter to thickness ratio, and the small size and close spacing or high density of individual hooks that are provided by the novel hook strip according to the present invention makes it able to easily firmly releasably engage loop material in shear, possibly because the many thin heads can easily move radially into engagement with rather small loops. Thus the hook strip according to the present invention is particularly useful for hook-and-loop fastening when the loops are provided by conventional knit or woven fabrics or random woven or non-woven materials which are not particularly adapted for use as the loop portions of hook and loop fasteners, and which are not as well engaged by known prior art hook strips. In general, the hooks are of uniform height, preferably of from about 0.10 to 1.27 mm in height, and more preferably from about 0.18 to 0.51 mm in height; have a density on the backing preferably of from 60 to 1,550 hooks per square centimeter, and more preferably from about 125 to 690 hooks per square centimeter; have a stem diameter adjacent the heads of the hooks preferably of from 0.076 to 0.635 mm, and more preferably from about 0.127 to 0.305 mm; have circular disc-like heads that project radially past the stems on each side preferably by an average of about 0.013 to 0.254 mm, and more preferably by an average of about 0.025 to 0.127 mm and have average thicknesses between their outer and inner surfaces (i.e., measured in a direction parallel to the axis of the stems) preferably of from about 0.013 to 0.254 mm and more preferably of from about 0.025 mm to 0.127 mm, with the heads having average head diameter (i.e., measured radially of the axis of the heads and stems) to average head thickness ratio preferably of from 1.5:1 to 12:1, and more preferably from 2.5:1 to 6:1.

For most hook-and-loop uses, the hooks of the novel mushroom-type hook strip should be distributed substantially uniformly over the entire area of the hook strip, usually in a square or hexagonal array. For hermaphroditic uses, the hooks preferably are distributed to prevent lateral slippage when engaged. See, for example, co-assigned U.S. Pat. No. 3,408,705 (Kayser et al), U.S. Pat. No. 4,322,875 (Brown), and U.S. Pat. No. 5,040,275 (Eckhardt et al).

To have both good flexibility and strength, the backing of the novel mushroom-type hook strip preferably is from 0.025 to 0.512 mm thick, and more preferably is from 0.064 to 0.254 mm in thick, especially when the hook strip is made of polypropylene or a copolymer of polypropylene and polyethylene. For some uses, a stiffer backing could be used, or the backing can be coated with a layer of pressure sensitive adhesive on its surfaces opposite the hooks by which the backing could be adhered to a substrate so that the backing could then rely on the strength of the substrate to help anchor the hooks.

The novel mushroom-type hook strip can be inexpensive because, using relatively inexpensive apparatus, it can be produced at higher line speeds than has been feasible for the manufacture of prior hook strips. The novel hook strip can be produced in long, wide webs that can be wound up as rolls for convenient storage and shipment. The hook strip in such rolls can have a layer of pressure sensitive adhesive on the surface of its backing opposite the hooks which can releasably adhere to the heads of the hooks on underlying wraps of the hook strip in the roll, thus not requiring a release liner to protect the layer of pressure sensitive adhesive in the roll while the limited area of the heads to which the pressure sensitive adhesive is adhered in the roll maintains the hook strip in the roll until it is ready for use, and then allows it to be easily unrolled from the roll. Pieces of desired lengths can be cut from a roll and adhesively or otherwise secured to articles such as a flap of a garment to permit the flap to be releasably fastened.

Virtually any orientable thermoplastic resin that is suitable for extrusion molding may be used to produce the novel mushroom-type hook strip. Thermoplastic resins that can be extrusion molded and should be useful include polyesters such as poly(ethylene terephthalate), polyamides such as nylon, poly(styrene-acrylonitrile), poly(acrylonitrile-butadiene-styrene), polyolefins such as polypropylene, and plasticized polyvinyl chloride. A preferred thermoplastic resin is a random copolymer of polypropylene and polyethylene containing 17.5% polyethylene and having a melt flow index of 30, that is available as SRD7-463 from Shell Oil Company, Houston, Tex.

BRIEF DESCRIPTION OF THE DRAWING

The invention will be further described with reference to the accompanying drawing wherein like parts are identified by like reference numerals in the several views, and wherein:

FIG. 1 is a cross section through a mushroom-type hook strip according to the present invention;

FIG. 2 is a cross section of interengaging pieces of the hook strip of FIG. 1;

FIGS. 6A & 6B diagram a method of making the hook strip of FIGS. 1 through 5.

FIG. 8 illustrates a roll of the hook strip of FIG. 1 having a layer of pressure sensitive adhesive on its backing which is adhered to heads on the hooks to retain the hook strip in the roll until it is withdrawn for adhesion to a substrate.

DETAILED DESCRIPTION OF THE INVENTION

Figure 3:
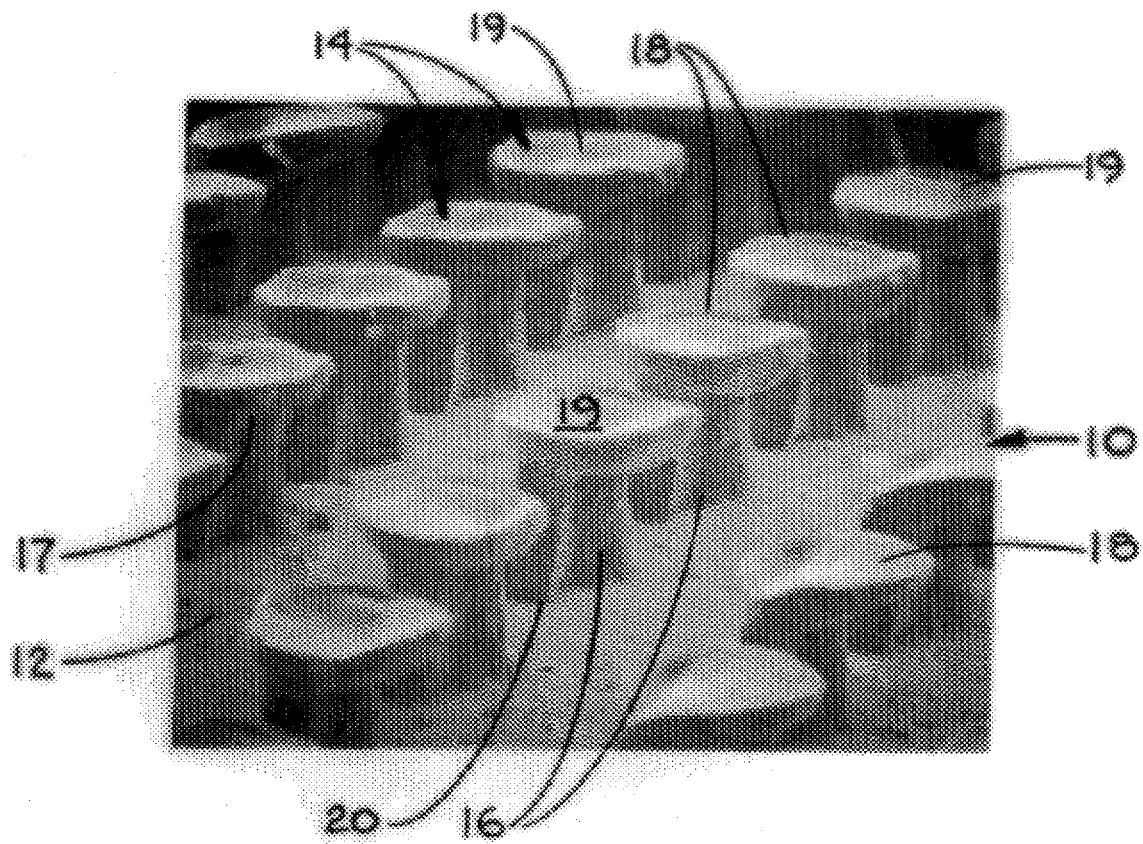
FIG. 3 is an enlarged photograph of the mushroom-type hook strip according to the present invention.

Referring now to the drawing, there is shown in FIGS. 1 through 5 a hook strip according to the present invention that is generally designated by the reference numeral 10.

The hook strip 10 has a substantially continuous planar backing 12 of thermoplastic resin. Integral with the backing 12 is an array of mushroom-shaped projections or hooks 14 projecting generally at right angles to one major surface of the backing 12. Each of the hooks 14 has a molecularly oriented stem 16 and, at the end of the stem 16 opposite the backing 12, a generally circular plate-like cap or head 18 projecting radially past or overhanging the stem 16 with a generally planar but slightly concave outer surface 19, and a generally planar radially extending inner surface 17 adjacent and parallel to the major surfaces of the backing 12. Preferably, the head 18 has a diameter to thickness ratio of greater than 1.5:1 (i.e., the diameter of the head 18 being its average maximum diameter measured radially of the head 18 and stem 16 and the thickness of the head 18 being its average maximum thickness measured between its outer and inner surfaces 19 and 17). The stem 16 can also have a fillet 20 around its base.

Figure 4:
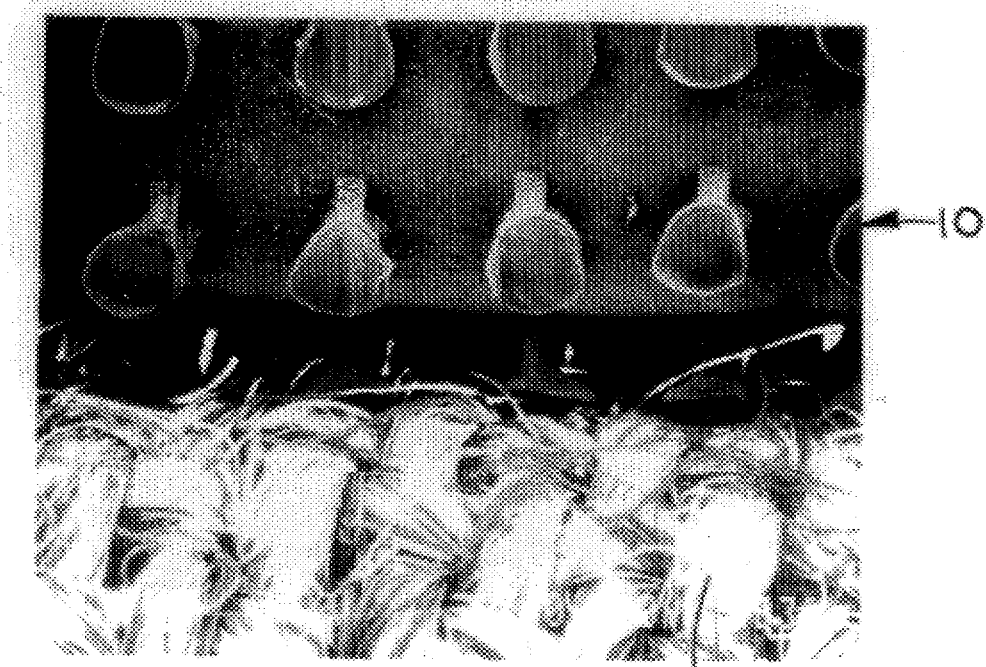
FIG. 4 is a photograph at lesser magnification of the mushroom-type hook strip of FIG. 3 adjacent a conventional woven fabric that provides a loop material with which the hook strip can be engaged.
Figure 5:
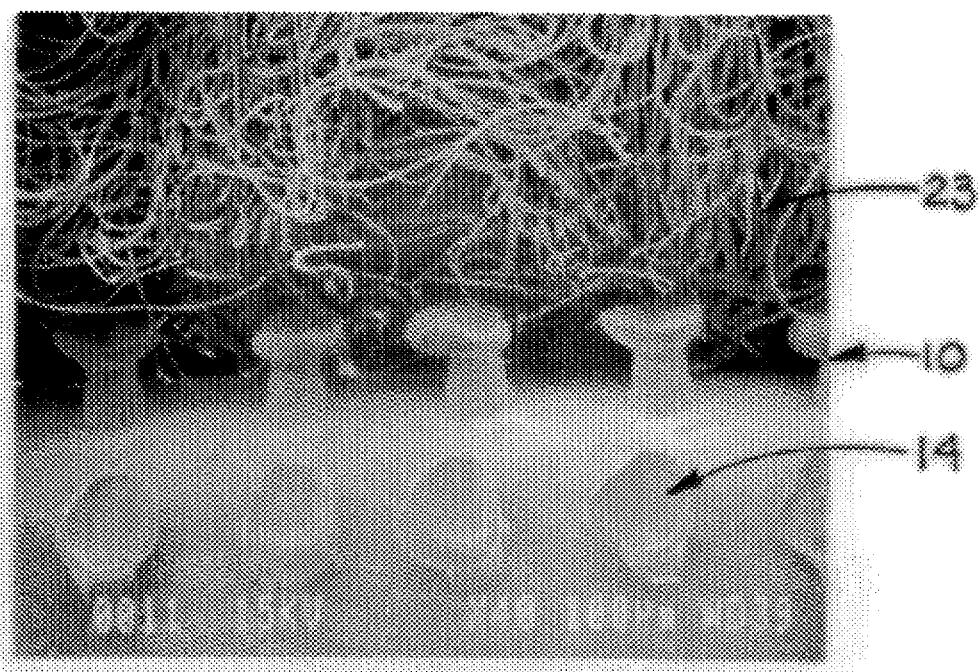
FIG. 5 is a photograph at lesser magnifications of the mushroom-type hook strip of FIG. 3 adjacent a conventional nonwoven material that provides a loop material with which the hook strip can be engaged.

A piece of the hook strip 10 can provide the hook portion of a hook-and-loop mechanical fastener, or it can be used to releasably engage a fabric which is penetratable by the mushroom-shaped hooks 14, such as the fabrics 22 and 23 shown respectively in FIGS. 4 and 5; the fabric 22 being the woven fabric commercially available under the trade designation Beachwood 2342000104 from Fabri-Centers of America, Inc., Hudson, Ohio; and the fabric 23 being the nonwoven material commercially available under the trade designation Versalon 140-093 hydroentangled rayon/PET from Veratec, Walpole, Mass.

Also, the hook strip 10 can be configured such that two pieces of the hook strip 10 can be interengaged to form a hermaphroditic mechanical fastener as shown in FIG. 2.

In FIG. 6A a feed stream 30 of thermoplastic resin is fed into an extruder 32 from which a heated resin melt is fed through a die 34 to a rotating cylindrical mold 36. Cavities 38 in the cylindrical continuous surface of the mold 36 are optionally evacuated by an external vacuum system 40. The die 34 has an output radius equal to that of the mold 36 in order to provide a seal between the die and the mold. Rapid flow of the resin into the mold cavities 38 induces molecular orientation parallel to the direction of flow, and the mold is water-cooled (cooling means not shown) to provide rapid quenching to freeze this orientation in place. The solidified resin is stripped from the mold 36 by a stripper roll 44 as a web 42 that has an array of upstanding stems 48. This web 42 can either be wound into a roll for storage or fed directly into the mushroom forming apparatus of FIG. 6B.

In FIG. 6B, the web 42 is fed through a gap at the nip between two calendar rolls 52a and 52b so that the roll 52a will contact predetermined portions of the distal ends of the stems 48. The roll 52a that contacts the stems 48 is heated so that it heats the tips of the stems to a temperature at which they will readily deform under mechanical pressure. Maintaining the tips at this temperature allows melting and molecular disorientation to take place. During such contact and/or upon subsequent cooling, the tips can be formed into the generally uniform disk shaped mushroom heads 18 shown in FIGS. 1 through 5, each having a substantially planer to slightly concave outer surface 19 and a larger cross section than the original stem 48.

Figure 7:
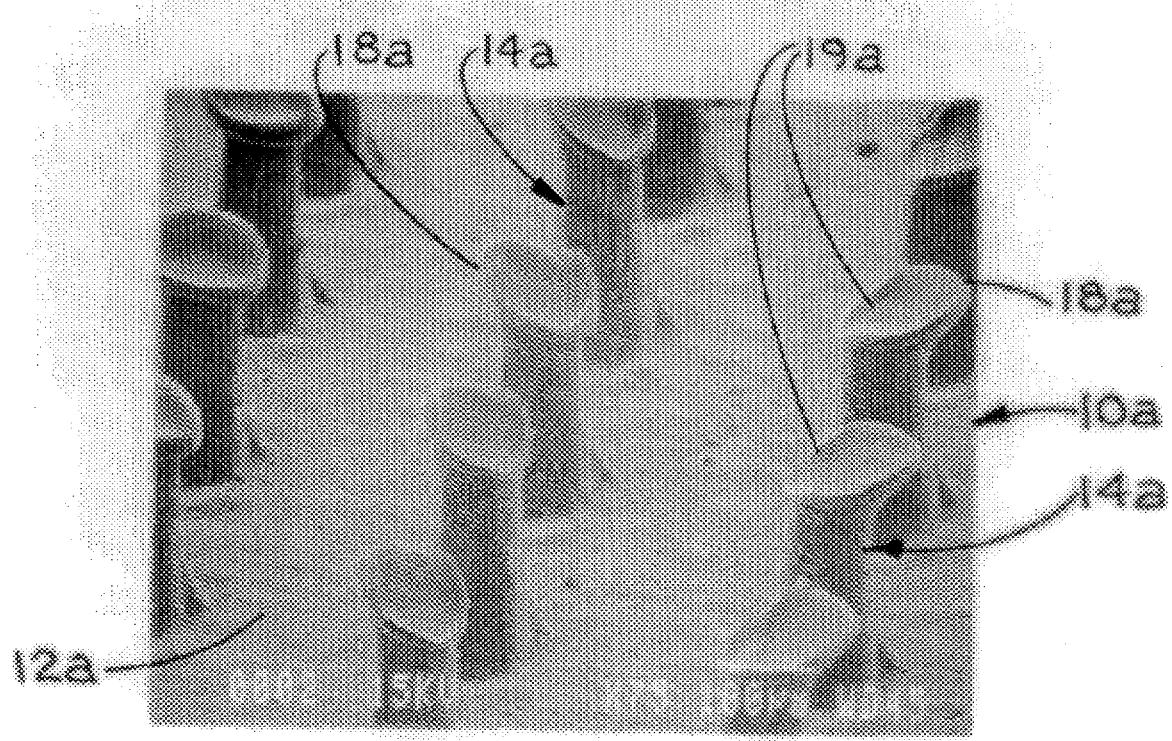
FIG. 7 is a photograph of a modification of the hook strip of FIG. 3.

The gap at the nip between the two calendar rolls 52a and 52b can be adjusted or decreased and/or the speed of the web 42 can be increased so that the heat transfer from the roll 52a is insufficient to deform the tips of the stems 48 with the stems 48 projecting at a right angle to the base of the web 42. Consequently, the stems 48, which are resiliently flexible, will bend axially with respect to the roll 52a as the heads are being formed, and after the heads leave contact with the roll 52a, the stems 48 will again return to their normal upright position normal to the base of the web 42. The heads 18a that have thus been formed will then be disposed as shown in FIG. 7 with the outer surfaces 19a of the heads 18a disposed at what appears to be angles of approximately 30 degrees with respect to the adjacent major surface of the backing 12a, rather than being disposed as shown in FIGS. 1 through 5 with the outer surfaces 19 of the heads 18 generally parallel to the adjacent major surface of the backing 12. It is believed that the gap at the nip between the two calendar rolls 52a and 52b could be adjusted or decreased and/or the speed of the web 42 increased to result in the outer surfaces 19a of the heads 18a being disposed at angles of up to at least 45 degrees with respect to the adjacent major surface of the backing 12a.

As can be seen in FIGS. 3 and 7, the outer surfaces 19 and 19a of the heads 18 and 18a (which we define as being generally planar) are somewhat irregular and slightly concave. By "the angles at which the outer (or inner) surfaces of the heads are disposed" we mean the angle at which flat surfaces placed in contact with and supported on the outer surfaces 19 or 19a of the heads 18 or 18a would be disposed with respect to another surface such as the adjacent major surface of the backing 12 or 12a.

FIG. 8 illustrates a roll 60 of the hook strip 10 of FIG. 1 having a layer 62 of pressure sensitive adhesive permanently adhered on the major surface of its backing 12 opposite the hooks 14. The layer 62 of pressure sensitive adhesive is releasably adhered to the outer surfaces 19 of the heads 18 on the hooks 14 in the underlying wraps of the hook material 10 on the roll 60 to retain the hook strip 10 in the roll 60 until it is withdrawn for application to a substrate. Thus, the layer 62 of adhesive on the hook strip 10 in the roll 60 does not require a release liner to protect it. The limited area of the heads 18 to which the layer 62 of adhesive in the roll 60 is adhered provides sufficient adhesion between the adhesive and the heads 18 to retain the hook strip 10 tightly wound on the roll 60 until it is intentionally unwound, while then allowing it to be easily unwound so that a length of the hook strip 10 can be removed from the roll 60. The outer surfaces of the heads provide good support for the wraps of the hook strip 10 in the roll 60 so that the roll 60 does not require flanges along its side surfaces to stop its wraps from telescoping axially of the roll 60. Desired lengths of the hook strip 10 can be unwound, cut from the roll 60 and adhesively secured to articles such as a portion of a garment (e.g., particularly including a portion of a disposable diaper or other disposable garment) to permit that portion to be releasably fastened to another portion of the garment.

EXAMPLE

An ethylene-propylene impact copolymer resin (#SRD7-463 available from Shell Chemical Co.) was extruded at a temperature of 260 degrees Centigrade into the cavities of a mold maintained at 93 degrees Centigrade while moving a continuous surface of the mold from which the cavities were recessed at a surface speed of 23 meters per minute. The mold had a square array of holes or cavities, approximately 0.64 mm apart in each direction along the surface of the mold (i.e., a density of 250 cavities per square centimeter). Each of the holes was approximately 0.2 mm in diameter and 1.78 mm deep. The equipment used differed from that illustrated in FIG. 6A in that the resin was pressed into the holes by a roller along the surface of the mold adjacent where the resin was extruded onto the mold and spaced from that surface so that the thickness of the layer of resin overlying the cavities and the surface of the mold was 0.09 mm. The solidified resin was stripped from the mold as a web having an array of upstanding stems approximately 0.47 mm long.

Using an apparatus of the type illustrated in FIG. 6B, the resultant web was run through a nip between two calendar rolls spaced by 0.2 mm at a speed of 3 meters per minute while the top roll that contacted the ends of the stems was maintained at a temperature of 140 degrees Centigrade. This produced the mushroom-type hook strip 10 pictured in FIG. 3. The hooks 14 had a cap or head 18 diameter of about 0.35 mm, an outer surface 19 area of about 0.10 mm$^2$, a head thickness between its outer and inner surfaces 19 and 17 of about 0.07 mm, and a head 18 overhang radially of the stem 16 of about 0.08 mm. The hook height (i.e., the height between the outer surface 19 of the head 18 and the adjacent surface of the backing 12) was about 0.28 mm and the stem diameter was about 0.20 mm. The hooks 14 on the hook strip 10 engaged the fibers on non-lofty, non-woven materials, knitted and woven fabrics and on nonwoven fiber layers of laminates that would not typically be considered useful as good loop fastener materials. That engagement restricted relative movement in shear (i.e., relative movement a direction parallel to the backing 12 of the hook strip 10 between the hook strip 10 and the fabrics or laminates with which its hooks 14 were engaged), while allowing the hooks 14 to be easily peeled from engagement from those fabrics or laminates.

Shear strength data was obtained using the Shear Test described below for engagement of the hooks 14 on the mushroom-type hook strip 10 with several such woven, knit and nonwoven fabrics, several laminates, and with a loop material intended for use as a portion of a hook and loop fastener; and for comparison, similar shear strength data was also obtained for engagement of a hook fastener commercially available under the trade designation #200 from Aplix Co., South Holland, Ill., with the same fabrics, laminates and loop material.

A comparison of the physical characteristics of the example hook strip material 10 and the Aplix #200 hook fastener (stock number MX25M000-H) is as follows:

|  | Example material | Aplix |
| --- | --- | --- |
| Head Diameter (mm) | 0.35 | 0.40 |
| Head outer surface Area (mm$^2$) | 0.10 | 0.13 |
| Head Overhang (mm) | 0.08 | 0.11 |
| Head Thickness (mm) | 0.07 | 0.26 |
| Hook Height (mm) | 0.28 | 0.81 |
| Stem Diameter (mm) | 0.20 | 0.18 |
| Backing Thickness (mm) | 0.09 | — |
| Hook Density (#/cm$^2$) | 250 | 105 |

(Note: In the Aplix hook fastener the mushroom hooks were inclined at an angle of roughly 40 degrees from a line normal to the major surfaces of its backing whereas the mushroom shaped hooks 14 of the example projected at essentially a right angle to the major surfaces of its backing 12.)

The resultant shear strength data obtained is as follows:

When tested in shear against a woven fabric of a type often used in clothing (i.e., a 50% polyester and 50% rayon woven fabric commercially available under the trade designation Beachwood 2342000104 from Fabri-Centers of America, Inc., Hudson, Ohio, the engagement in shear of the Example hook strip 10 with the fabric was about 46 grams per square centimeter when the shear was in the machine or warp direction of the fabric, and was about 94 grams per square centimeter when the shear was in the cross or weft direction of the fabric, whereas the engagement in shear of the Aplix hook fastener with the fabric was about 23 grams per square centimeter when the shear was in the machine or warp direction of the fabric, and was about 16 grams per square centimeter when the shear was in the cross or weft direction of the fabric.

When tested in shear against another woven fabric of a type often used in clothing (i.e., a 50% polyester and 50% rayon woven fabric commercially available under the trade designation Beachwood 1817300994 from Fabri-Centers of America, Inc., the engagement in shear of the Example hook strip 10 with the fabric was about 29 grams per square centimeter when the shear was in the machine or warp direction of the fabric, and was about 49 grams per square centimeter when the shear was in the cross or weft direction of the fabric; whereas the engagement in shear of the Aplix hook fastener with the fabric was about 10 grams per square centimeter when the shear was in the machine or warp direction of the fabric, and was about 0 grams per square centimeter when the shear was in the cross or weft direction of the fabric.

When tested in shear against a knit fabric of a type often used in clothing (i.e., a 100% acrylic fabric knit fabric commercially available under the trade designation Beachwood 6111200301 from Fabri-Centers of America, Inc., the engagement in shear of the Example hook strip 10 with the fabric was about 45 grams per square centimeter when the shear was in the machine or warp direction of the fabric, and was about 69 grams per square centimeter when the shear was in the cross or weft direction of the fabric; whereas the engagement in shear of the Aplix hook fastener with the fabric was about 17 grams per square centimeter when the shear was in the machine or warp direction of the fabric, and was about 21 grams per square centimeter when the shear was in the cross or weft direction of the fabric.

When tested in shear against a non-woven laminate of a type often used in disposable garments (e.g., disposable diapers (i.e., a 0.5 ounce polypropylene non-woven fiber layer laminated to a 0.04 mm thick polypropylene film, which non-woven fiber layer is commercially available under the trade designation "Celestra" from Fiberweb, Chicago, Ill., the engagement in shear of the Example hook strip 10 with the fiber layer on the laminate was about 293 grams per square centimeter when the shear was in the machine direction of the laminate, and was about 171 grams per square centimeter when the shear was in the cross direction of the laminate; whereas the engagement in shear of the Aplix hook fastener with the fiber layer was about 65 grams per square centimeter when the shear was in the machine direction of the laminate, and was about 116 grams per square centimeter when the shear was in the cross direction of the laminate.

When tested in shear against another non-woven laminate of a type also often used in disposable garments (i.e., a 0.5 ounce spunbond polypropylene non-woven fiber layer laminated to a 0.04 mm thick polypropylene film, which non-woven fiber layer is commercially available from Dow & Low, Scotland, the engagement in shear of the Example hook strip 10 with the fiber layer of the laminate was about 221 grams per square centimeter when the shear was in the machine direction of the laminate, and was about 254 grams per square centimeter when the shear was in the cross direction of the laminate; whereas the engagement in shear of the Aplix hook fastener with the fiber layer of the laminate was about 51 grams per square centimeter when the shear was in the machine direction of the laminate, and was about 59 grams per square centimeter when the shear was in the cross direction of the laminate.

When tested in shear against a non-woven material of a type often used as industrial wiping material (i.e., a hydroentangled rayon/PET non-woven material commercially available under the trade designation Versalon 140-093 from Veratec) the engagement in shear of the Example hook strip 10 with the non-woven material was about 257 grams per square centimeter; whereas the engagement in shear of the Aplix hook fastener with the non-woven material was about 74 grams per square centimeter.

When tested in shear against another non-woven material of a type often used in garments (i.e., a spunbond polypropylene non-woven material commercially available under the trade designation RFX 9.585A from Amoco, Atlanta, Ga.) the engagement in shear of the Example hook strip 10 with the non-woven material was about 107 grams per square centimeter; whereas the engagement in shear of the Aplix hook fastener with the non-woven material was about 45 grams per square centimeter.

When tested in shear against another non-woven material of a type used for the tie strings in face masks (i.e., a non-woven web of 1 and ½ denier polypropylene fibers that are carded and calendered to provide 20% bonded area that is made by Minnesota Mining and Manufacturing Company, St. Paul, Minn.) the engagement in shear of the Example hook strip 10 with the non-woven material was about 195 grams per square centimeter; whereas the engagement in shear of the Aplix hook fastener with the non-woven material was about 2 grams per square centimeter.

When tested in shear against a loop material sold for use as the loop portion of hook and loop fasteners (i.e., the loop material commercially available under the trade designation loop stock number MX25L000-H from Aplix), the engagement in shear of the Example hook strip 10 with the loop material (after the backing 12 of the hook strip 10 was reinforced with number 355 packaging tape available from Minnesota Mining and Manufacturing Company) was about 1369 grams per square centimeter; whereas the engagement in shear of the Aplix hook fastener with the loop material was about 1147 grams per square centimeter.

TESTING

Shear Strength Test

The shear strength test method used in obtaining the above values was a modified version of ASTM D5169-91, Mode 1. The shear strength was measured using an Instron™ Model 1122 tensile tester. The hook strips and the fabrics, laminates non-wovens or loop material to be tested were each cut into sample pieces 102 mm long by 25 mm wide. The sample pieces were conditioned by allowing them to come to equilibrium for 24 hours at "room conditions" or 21 degrees Centigrade and 45% relative humidity. The sample pieces of hook strips were laid on a support surface with the hooks projecting upwardly and the sample pieces of fabrics, laminates, non-wovens or loop material to be tested were placed with their surfaces to be engaged down on top of the hook strips such that the areas of overlap between the sample hook strips and those sample pieces were each 51 mm long by 25 mm wide. A 5 kilogram roller was rolled over the portions of the sample pieces engaged with each other 5 times in each direction or a total of 10 times. Free ends of the engaged hook strips and sample pieces of fabric, laminate, non-woven or loop material were then each placed in the jaws of the tensile tester so that the line along which shear was to be tested was parallel to and centered along the direction of movement of the jaws. The jaws were moved apart at a crosshead speed of 300 mm per minute to separate the engaged hook strip and sample piece of fabric, laminate, nonwoven or loop material, and a pen and chart recorder recorded the maximum force required to cause shear of the engagement therebetween during such separation. The shear strength values reported are an average of three such tests.

Birefringence

Birefringence can be measured by any of several different optical techniques, such as by using standard fluids with different indices of refraction, the Becke line technique, dispersion staining, or a compensator. The compensator technique was used to obtain the birefringence measurement of the Example hook strip 10 described above which was found to be 0.003.

Using an "Ortholux 2 Pol" polarized light microscope with a Berek compensator from E. Leitz Company, Covington, Ky., a hook strip is placed under crossed polarized light with its z-axis oriented north-south. The microscope stage is rotated 45 degrees. A compensator is rotated in each direction until a black fringe appears; at this point retardations are equal and opposite. Compensator readings are recorded and the birefringence of the sample is calculated according to the equation:

$$B = R \times C/t$$

where R=retardation, C=compensator constant, and t=sample thickness. The retardation R, is defined as the phase difference between the two components in numbers of waves.

We claim:

1. A method for making a mushroom-type hook strip having a backing, an integral array of upstanding stems having heads at ends of the stems opposite the backing, and a predetermined finished thickness dimension between a first major surface of the backing opposite the stems and outer surfaces on the heads opposite the backing, said method comprising the steps of
    a) providing a mold which has cavities recessed from a continuous surface that are negatives of said array of upstanding stems,
    b) moving the continuous surface of the mold along a predetermined path,
    c) continuously injecting a molten, molecularly orientable thermoplastic resin into the cavities in excess of an amount that would fill the cavities, which excess forms a layer of resin overlying the cavities and the continuous surface around the cavities,
    d) causing the molten resin to become molecularly oriented while it fills the cavities,
    e) allowing the injected resin to solidify,
    f) continuously stripping from the mold the solidified resin layer as a web including the backing and the integral array of upstanding stems which have tips at the ends of the stems opposite the backing, the backing of the web having a second major surface adjacent the stems and opposite said first major surface of the backing opposite the stems, and the web having a predetermined initial thickness dimension between the first major surface of the web opposite the stems and the tips of the stems that is greater than said finished thickness dimension, and
    g) continuously passing the web at a set rate through a gap having a dimension less than said predetermined finished thickness dimension between a support surface along the first major surface of the backing opposite the stems and a heated surface parallel to the support surface and adjacent the tips of the stems opposite the backing to compress the stems against said heated surface, said rate, gap dimension, and the heating capacity of said heated surface being selected to cause heat transfer from the heated surface into the compressed stems sufficient to deform portions of the stems adjacent the tips of the stems into circular disc shaped mushroom heads having generally planar outer surfaces on the heads opposite the backing.

2. A method according to claim 1 wherein the dimension of said gap causes said step of continuously passing to include the step of resiliently deflecting said stems as they are moved through said gap so that after the web has passed through the gap the outer surfaces of said heads are disposed at an angle of up to about 45 degrees with respect to the second major surface of the backing adjacent the stems.

3. A method for making a mushroom-type hook strip employing a mold which has cavities recessed from a continuous surface that are negatives of an array of upstanding stems, said method comprising the steps of
    a) moving the continuous surface of the mold along a predetermined path,
    b) continuously injecting a molten, molecularly orientable thermoplastic resin into the cavities in excess of an amount that would fill the cavities, which excess forms a layer of resin overlying the cavities and the continuous surface around the cavities,
    c) allowing the injected resin to solidify,
    d) continuously stripping from the mold the solidified resin layer as a web including a backing and an integral array of upstanding stems having tips at ends of the stems opposite the backing, the backing having a major surface adjacent the stems, and an opposite major surface opposite the stems,
    e) deforming portions of the stems adjacent the tips by contact with a heated surface to produce a circular disc shaped mushroom head having an outer surface at the end of each stem opposite the backing, and
    f) resiliently deflecting the stems during said deforming step so that after said deforming step the outer surfaces of the heads are disposed at an angle of up to about 45 degrees with respect to the major surface of the backing adjacent the stems.

4. A method for making a mushroom-type hook strip that can be used in a hook and loop mechanical fastener and has a backing, an integral array of upstanding stems having heads at ends of the stems opposite the backing, and a predetermined finished thickness dimension between a first major surface of the backing opposite the stems and outer surfaces on the heads opposite the backing, said method comprising the steps of
    a) providing a mold which has cavities recessed from a continuous surface that are negatives of said array of upstanding stems at a stem density of over 60 stems per square centimeter,
    b) moving the continuous surface of the mold along a predetermined path,
    c) continuously injecting a molten, molecularly orientable thermoplastic resin into the cavities in excess of an amount that would fill the cavities, which excess forms a layer of resin overlying the cavities and the continuous surface around the cavities, d) causing the molten resin to become molecularly oriented while it fills the cavities as evidenced by a birefringence value of at least 0.001, e) allowing the injected resin to solidify, f) continuously stripping from the mold the solidified resin layer as a web including the backing and the integral array of upstanding stems which have tips at the ends of the stems opposite the backing, the backing of the web having a second major surface adjacent the stems and opposite said first major surface of the backing opposite the stems, and the web having a predetermined initial thickness dimension between the first major surface of the web opposite the stems and the tips of the stems that is greater than said finished thickness dimension, and g) continuously passing the web at a set rate through a gap having a dimension less than said predetermined finished thickness dimension between a support surface along the first major surface of the backing opposite the stems and a heated surface parallel to the support surface and adjacent the tips of the stems opposite the backing to compress the stems against said heated surface, said rate, gap dimension, and the heating capacity of said heated surface being selected to cause heat transfer from the heated surface into the compressed stems sufficient to deform portions of the stems adjacent the tips of the stems into circular disc shaped mushroom heads having generally planar outer surfaces on the heads opposite the backing and having inner surfaces adjacent the backing generally parallel to said outer surfaces.

5. A method according to claim 4 wherein said providing, moving, continuously injecting, causing, allowing and continuously stripping steps provide a negative array of stems having diameters in the range of about 0.076 to 0.635 mm, and said continuously passing step provides a gap that forms heads having average thicknesses between said outer and inner surfaces in the range of about 0.013 mm to 0.254 mm, which heads overhang said stems an average in the range of about 0.013 to 0.254 min.

6. A method according to claim 4 wherein said providing, moving, continuously injecting, causing, allowing and continuously stripping steps provide a negative array of stems having a density of over 125 stems per square centimeter and diameters in the range of about 0.127 to 0.305 mm, and said continuously passing step provides a gap that forms heads having average thicknesses between said outer and inner surfaces in the range of about 0.025 mm to 0.127 mm, which heads overhang said stems an average in the range of about 0.025 to 0.127 mm.

7. A method according to claim 4 wherein said providing, moving, continuously injecting, causing, allowing and continuously stripping steps provide a negative array of stems having a density of at least about 250 stems per square centimeter and diameters in the range of about 0.127 to 0.254 mm, and said continuously passing step provides a gap that forms heads having average thicknesses between said outer and inner surfaces of about 0.07 mm, which heads overhang said stems an average of about 0.08 mm.

8. A method according to claim 4 wherein the dimension of said gap causes said step of continuously passing to form heads having outer surfaces that are generally parallel to the adjacent surface of said backing.

9. A method according to claim 4 wherein the dimension of said gap causes said step of continuously passing to include the step of resiliently deflecting said stems as they are moved through said gap so that after the web has passed through the gap the outer surfaces of said heads are disposed at an angle of up to about 45 degrees with respect to the second major surface of the backing adjacent the stems.

* * * * *